US 6,694,981 B2

(12) United States Patent
Gingles et al.

(10) Patent No.: US 6,694,981 B2
(45) Date of Patent: Feb. 24, 2004

(54) SURGICAL DRAPE

(75) Inventors: Bruce Gingles, Bloomington, IN (US); Daniel J. Sirota, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 10/196,313

(22) Filed: Jul. 16, 2002

(65) Prior Publication Data

US 2003/0121522 A1 Jul. 3, 2003

Related U.S. Application Data

(60) Provisional application No. 60/344,219, filed on Dec. 27, 2001.

(51) Int. Cl.[7] ............................................... A61B 19/00
(52) U.S. Cl. ....................................... 128/849; 128/853
(58) Field of Search ................... 128/849–853

(56) References Cited

U.S. PATENT DOCUMENTS

| 3,669,106 | A | * | 6/1972 | Schradins | 128/853 |
|---|---|---|---|---|---|
| 3,695,260 | A | * | 10/1972 | Endrns | 128/853 |
| 4,024,862 | A | * | 5/1977 | Collins | 128/853 |
| D256,161 | S | | 7/1980 | Oliver | |
| 4,730,609 | A | * | 3/1988 | McConnell | 128/853 |
| 5,002,070 | A | | 3/1991 | Taylor | |
| D333,404 | S | | 2/1993 | Thompson | |
| 5,538,012 | A | * | 7/1996 | Wiedner et al. | 128/849 |
| 5,901,706 | A | | 5/1999 | Griesbach et al. | |
| 6,298,855 | B1 | * | 10/2001 | Baird | 128/849 |
| 6,314,959 | B1 | | 11/2001 | Griesbach et al. | |
| 6,382,212 | B1 | | 5/2002 | Borchard | |

* cited by examiner

Primary Examiner—Michael A. Brown
(74) Attorney, Agent, or Firm—Brinks Hofer Gilson & Lione

(57) ABSTRACT

The present invention is directed toward a surgical drape having a base sheet and an absorbent sheet with at least one opening. A transparent or clear sheet is attached to the edges of the opening and has at least one fenestration for performing surgery when the drape is covering a patient.

22 Claims, 3 Drawing Sheets

SURGICAL DRAPE

This application claims the benefit of Provisional application Ser. No. 60/344,219, filed Dec. 27, 2001.

FIELD OF THE INVENTION

The present invention relates to a drape used in performing surgery, and in particular, to a surgical drape with a clear portion and an absorbent border.

BACKGROUND

Drapes are used during procedures to create and maintain a sterile environment about the surgical site. Draping materials are selected to create and maintain an effective barrier that minimizes the passage of microorganisms between non-sterile and sterile areas. To be effective, a barrier material should be resistant to blood, aqueous fluid, and abrasion, as lint-free as possible and drapable. When used during surgery, drapes prevent blood and other bodily fluids from contaminating the sterile field.

Many surgical drapes were originally made of cotton or linen, and were sterilized after each use for reuse. More recently, disposable drapes have been introduced, in which non-woven paper or fabric forms a substantial part of the drape. Many disposable drapes include a number of layers of different materials for the drape area and reinforcement area, with each layer providing a different property to the drape. For example, spun-bond fabrics, melt-blown fabrics, and polymer films have been used as layers in disposable drapes.

Surgical drapes will commonly have an opening or aperture (more commonly known in the medical field as a "fenestration") through which the surgical procedure is performed. In certain procedures, more than one surgical site is used. In these more complex procedures, the patient must be draped using a plurality of drapes or must be re-draped between procedures.

An adhesive material may be attached to the periphery of the drape material so that the drape can be held in place around the surgical site and so that blood will not pass between the drape and the patent's body. The combination of the drape itself and the adhesive material around the perimeter of the aperture ensures a barrier between the surgical wound and the remainder of the body.

It is desirable to form surgical drapes with absorbent material to absorb blood and other fluids during surgery. The absorbent material is usually placed on a opposite surface of the drape surface in contact with the patient's body. However, drapes having an absorbent material are generally opaque and therefore provide little visibility around the perimeter of the fenestration. Drapes with a transparent material do not provide adequate absorption of fluids. Therefore to minimize the risks associated with surgical procedures, it is desirable to provide a one-piece drape that is easy to apply and provides adequate visibility and absorption.

BRIEF SUMMARY

In response to the foregoing problems and difficulties encountered by those of skill in the art, the present invention is directed toward a surgical drape for covering a patient during a surgical procedure.

In one aspect, the invention includes a surgical drape that has a base sheet having an upper surface, a lower surface and at least one opening. An absorbent sheet is positioned on the upper surface of the base sheet and has at least one opening aligned with the opening of the base sheet. A transparent sheet is attached to the opening and has a fenestration through which a surgical procedure may be performed when the drape is covering a patient. The absorbent sheet is preferably formed from non-woven spunbond fabric. The base sheet is preferably formed from woven reusable fabrics or non-woven disposable fabrics. The transparent sheet is preferably hydrophobic and is formed from a low-density polyethylene film. The surgical drape may also have a layer of adhesive on a lower surface of the transparent sheet substantially surrounding the fenestration. A release liner may be placed on the adhesive layer.

In another aspect the invention includes a surgical drape having an opaque absorbent sheet having at least one opening. A clear sheet is attached to the opening, wherein the clear sheet has a fenestration and an adhesive coating on at least a portion of the clear sheet surrounding said fenestration. A release liner is on the adhesive coating.

In yet another aspect, the invention includes a surgical drape having an absorbent outer layer with at least one opening. An inner layer adapted to contact a patient. The inner layer has at least one opening aligned with the opening of said absorbent outer layer. A transparent sheet with at least one fenestration is attached to the at least one opening Other objects, features and advantages of the present invention will become apparent from the following detailed description. It should be understood, however, that the detailed description and the specific examples, while indicating embodiments of the invention, are given by way of illustration only, the invention being defined only by the claims following this detailed description.

BRIEF DESCRIPTION OF SEVERAL VIEWS OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1:
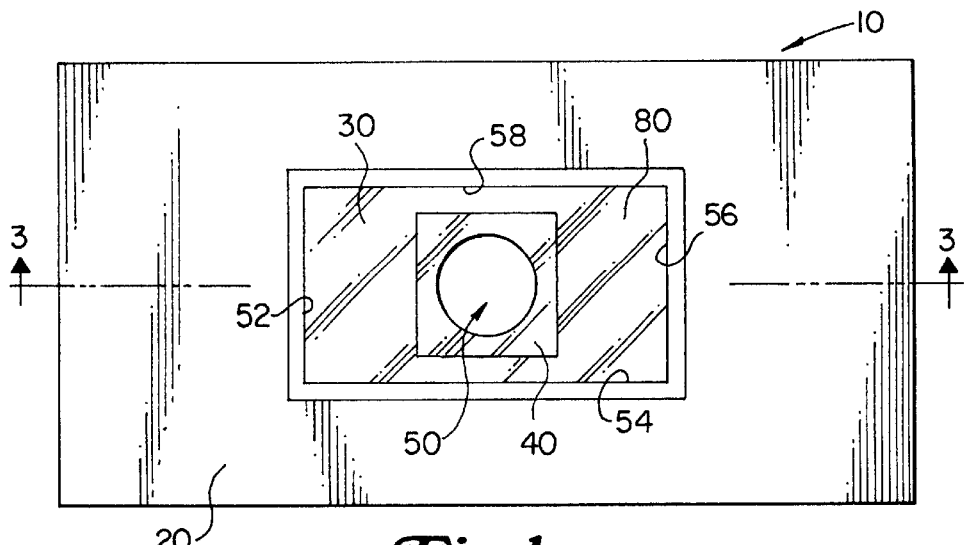
FIG. 1 is a top view of an embodiment of the drape according to the present invention.
Figure 2:
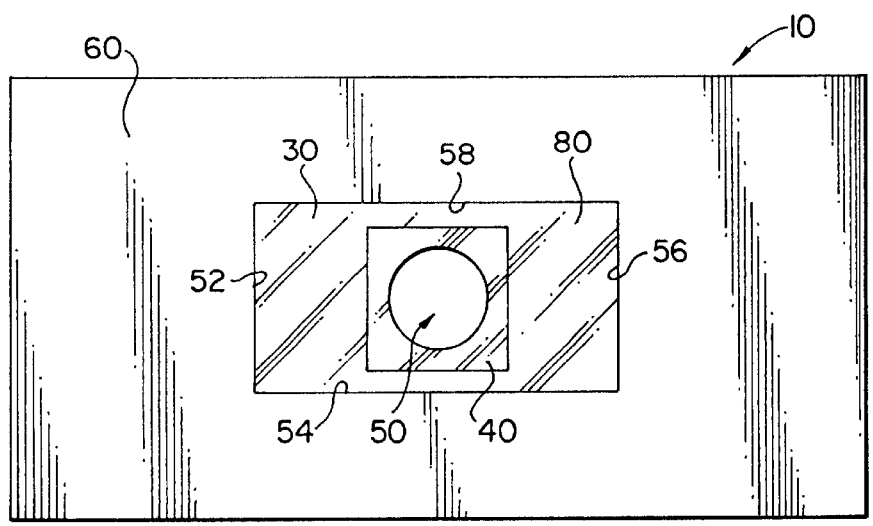
FIG. 2 is a bottom view of the drape illustrated in FIG. 1.

The present invention is directed toward a drape suitable for use in surgical procedures. One embodiment of the surgical drape 10 of the present invention is illustrated in FIG. 1. The surgical drape 10 includes a base sheet 60 (as illustrated in FIG. 2), an absorbent sheet 20, a transparent sheet 30, an opening or fenestration 50, and a release liner 40, the base sheet 60 having an upper surface 62 and a lower or patient-contacting surface 64. Although the drape may have varying dimensions and shapes, surgical drape 10 is normally rectangular and sized to cover at least a majority of a patient's body during a surgical procedure.

Figure 3:
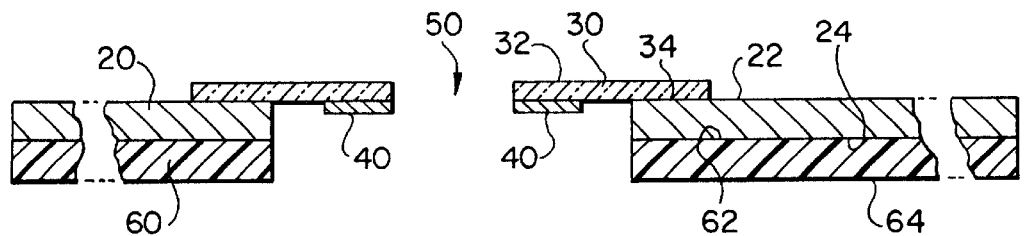
FIG. 3 is a cross-sectional view of the embodiment of the drape illustrated in FIG. 1 taken along line 3—3.

As illustrated in FIG. 3, the base sheet 60 has an upper surface 62 and a lower or patient-contacting surface 64. The base sheet may be made from a variety of materials, including, for example, woven, reusable fabrics and non-woven disposable fabrics or webs. Non-woven materials suitable for use with the present invention include, for example, multilayer laminates such as a spunbonded/meltblown/spunbonded ("SMS") material. The base sheet 60 is preferably a polyethylene film that is opaque and is impervious to liquid. An example of a polyethylene film used in forming the base sheet is the FT-200's, FT-300's, FT-500's and FT-700's polyethylene films available from Filmtech Corp. of Allentown, Pa.

As used herein, the term "non-woven fabric or web" means a web having a structure of individual fibers or threads that are interlaid, but not in an identifiable manner as in a knitted fabric. Non-woven fabrics or webs have been formed from many processes such as for example, melt-blowing processes, spunbonding processes, and bonded carded web processes.

As used herein, the term "spunbonded fibers" refers to small diameter fibers which are formed by extruding thermoplastic material as filaments from a plurality of fine, usually circular capillaries of a spinneret with the diameter of the extruded filaments then being rapidly reduced. The term "meltblown fibers" means fibers formed by extruding a thermoplastic material through a plurality of fine, usually circular, die capillaries as molten threads or filaments into converging high velocity, usually hot, gas streams which attenuate the filaments of molten material to reduce their diameter. Thereafter, the meltblown fibers are carried by the high velocity gas stream and are deposited onto a collective surface.

Referring to FIGS. 1 and 3, the absorbent sheet 20 has an upper surface 22 and a lower surface 24. The lower surface 24 of absorbent sheet 20 is superimposed on and affixed in some manner to the upper surface 62 of base sheet 60. A variety of attachment mechanisms may be used to secure the absorbent sheet 20 to the upper surface 62 of base sheet 60, such as, for example, adhesive, stitching, thermal or ultrasonic bonding. The absorbent upper surface 22 of absorbent sheet 20 remains exposed and available to absorb fluids emitted from the surgical site. The absorbent sheet 20 may be formed from a variety of fluid absorbing materials known in the art. Preferably, the absorbent sheet 20 is formed from a non-woven spunbond fabric such as the Dexter 13887 Absorbent Towel available from Webster Enterprises. The Absorbent Towel is a highly absorbent nownwoven material that maintains strength and uniformity even when wet. It can be resterilized using either gamma, ETO or steam.

In some embodiments, the upper surface 22 of absorbent sheet 20 may have an increased coefficient of friction to provide a slip-resistant surface to lessen the likelihood of undesired movement of surgical instruments that are placed upon the absorbent sheet 20. The absorbent sheet 20 also helps to inhibit penetration of the drape 10 by instruments that are placed on top of the absorbent sheet 20 during surgery. The absorbent sheet is also generally opaque and is preferably a shade of blue.

The absorbent sheet 20 and base sheet 60 have an common opening 80 defined by surfaces 52, 54, 56, and 58. Although the opening 80 illustrated in the present application is rectangular, it should be noted that said opening may be of any shape or size, so long as the longest and widest part of the opening are smaller than the longest and widest part of the absorbent sheet 20 and base sheet 60. The shape and size of the opening 80 is determined based on the size and area of the surgical site.

A transparent sheet 30 is attached to the edges 52, 54, 56 and 58. In a preferred embodiment the transparent sheet 30 is attached to the upper surface 22 of absorbent sheet 20, as illustrated in FIG. 3. However, the transparent sheet 30 may also be attached on the lower surface 62 of base sheet 60 or may be attached between the absorbent sheet 20 and the base sheet 60. A variety of attachment mechanisms may be used to secure the transparent sheet 30 to the upper surface 22 of absorbent sheet 20, such as, for example, adhesive, stitching, thermal or ultrasonic bonding. The transparent sheet 30 is made from a clear plastic or polymer material and is preferably formed from a low-density polyethylene film. The transparent sheet is generally hydrophobic and provides greater visibility of the surgical site during surgery. The transparent sheet 30 also provides visibility of the portion of the patient's body surrounding the surgery site. These areas are generally hidden in drapes found in the prior art, where an opaque absorbent sheet surrounds the fenestration.

The transparent sheet 30 has a fenestration 50, as illustrated in FIGS. 1–3. The fenestration 50 is circular in shape. However, it is contemplated that the fenestration utilized in the present invention may have various other shapes, such as a square, rectangle, or a polygon.

The fenestration 50 is positioned within the transparent sheet 30 so that, when the drape 10 is applied to the patient, the fenestration 50 is disposed over the surgical site. Adhesive material is positioned around the periphery of the fenestration 50 on the lower surface of the transparent sheet 30 to adhere the periphery of the fenestration 50 to the patient. The tacky and pressure-sensitive adhesives used may be of any biologically acceptable adhesive. Examples of such adhesive materials are described in U.S. Pat. No. 3,669,106 entitled "Surgical Drape with Adhesive Attachment Means" to Schrading et. al, which is incorporated herein in its entirety by reference.

To facilitate handling of the surgical drape 10 and to maintain the sterility of the transparent sheet, the adhesive surface may be covered with a release liner 40. The release liner 40 may be formed of any of a wide variety of materials which are commonly available. For example, wax- or silicone-coated papers may be placed over the adhesive side of the incise layers until the drape 10 is applied to the patient. Alternate materials may also be utilized, such as, for example, plastic materials having at least one non-adherent surface. Such materials may be utilized when a tear-resistant release liner is appropriate. Additionally the release liner 40 may be segmented into multiple to facilitate application of the drape 10 to the patient. Thus, the medical personnel applying the drape 10 to the patient may remove one segment of the release liner 40 at a time. This enables the medical personnel to handle a smaller exposed area of adhesive at one time, reducing the opportunities for contamination or creasing of the exposed incise layer.

Figure 4:
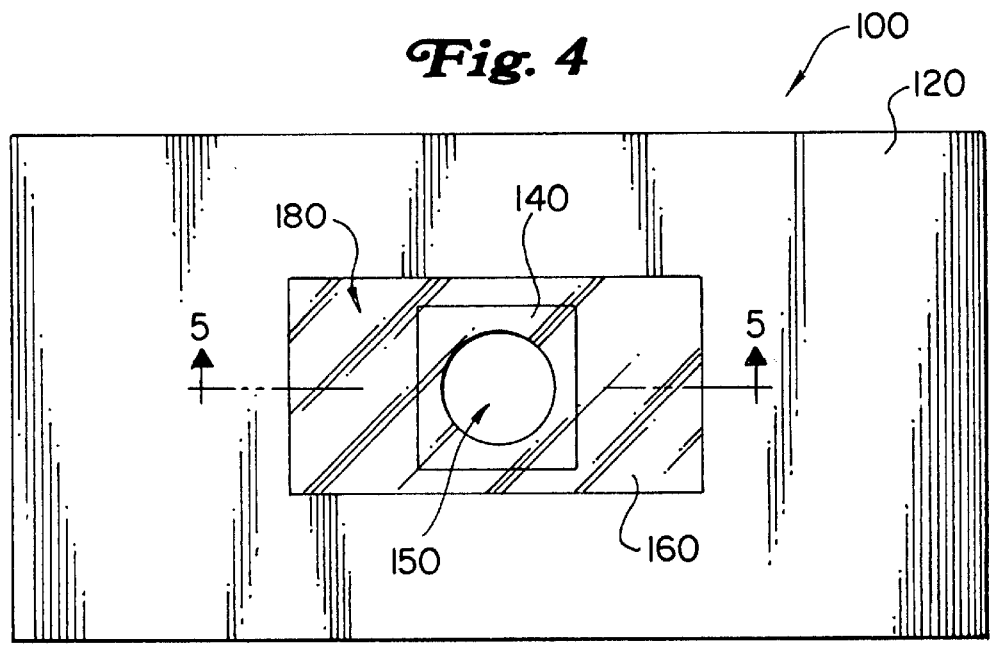
FIG. 4 is a top view of another embodiment of the drape according to the present invention.
Figure 5:
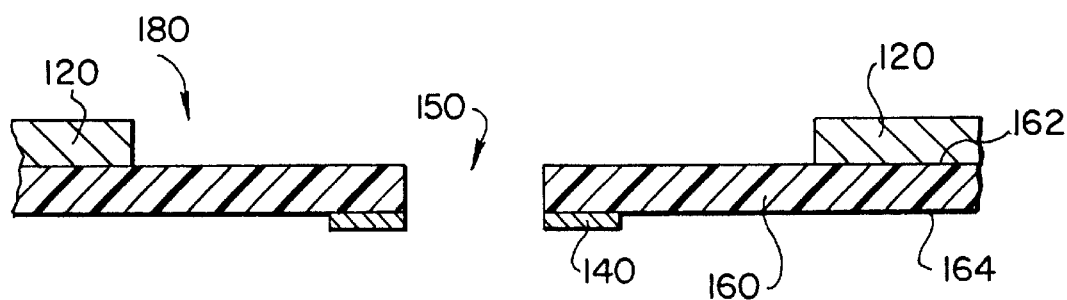
FIG. 5 is a cross-sectional view of the embodiment of the drape illustrated in FIG. 4 taken along line 5—5.

FIGS. 4 and 5 illustrate an alternate embodiment of a surgical drape 100. Drape 100 is essentially formed from two layers. A clear base sheet 160 has an upper surface 162 and a lower patient contacting surface 164. The base sheet 160 is preferably formed from a polyethylene material similar to the base sheet 60. The base sheet 160 has a fenestration 150. The fenestration 150 is positioned within the base sheet 160 so that, when the drape 100 is applied to the patient, the fenestration 150 is disposed over the surgical site. Adhesive material is positioned around the periphery of the fenestration 150 on the lower surface of the base sheet 160 to adhere the periphery of the fenestration 150 to the patient. A release liner 140 may be placed on the adhesive area.

An absorbent sheet 120 having an opening 180 is attached to the upper surface 164 of base sheet 160. The opening 180 is aligned so that fenestration 150 is exposed. Preferably, opening 180 is large enough so that portions of base sheet 160 are also exposed, thereby providing visibility of the portion of the patient's body surrounding the surgery site.

Figure 6:
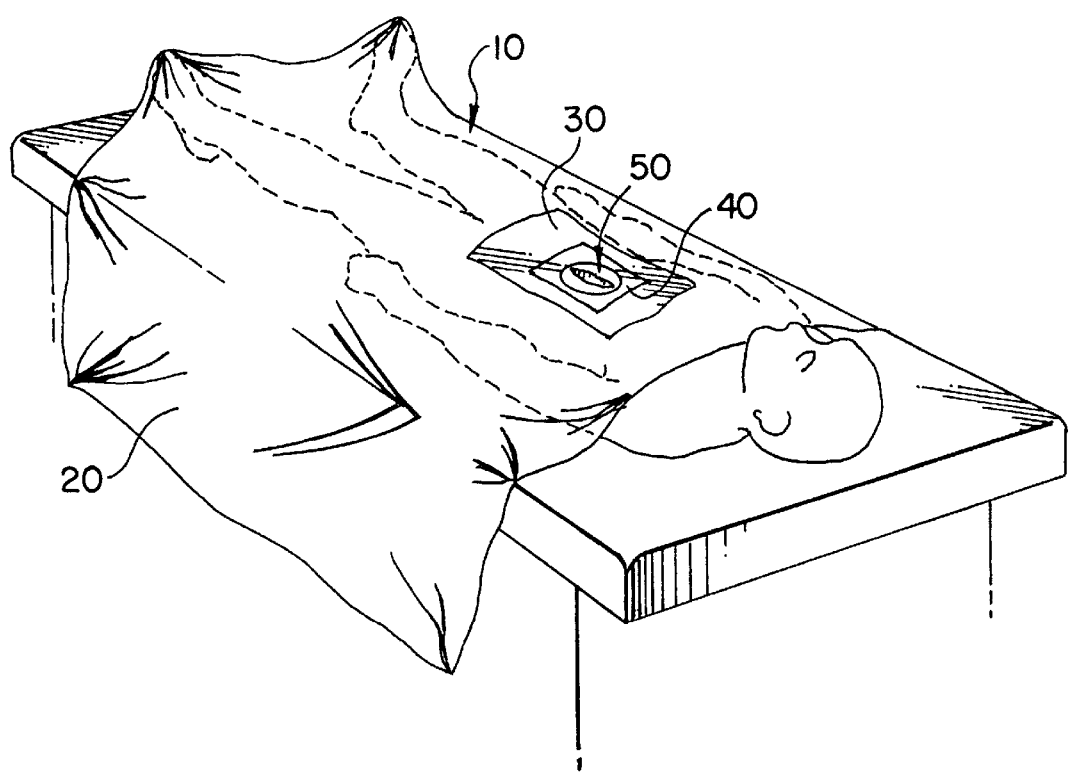
FIG. 6 is a top view of the drape illustrated in FIG. 1 disposed on a patient as used in surgery.

FIG. 6 illustrates a surgical drape that is placed on a patient. Directions may be stamped, printed or adhered to the drape to indicate how the drape is to be placed on the patient. For example, arrows (not shown) as well as other diagrams and/or instructions may be utilized and applied to any portion of the surgical drape in any of a wide variety of manners.

It is contemplated that numerous modifications may be made to the surgical drape of the present invention without departing from the spirit and scope of the invention as defined in the claims. For example, while the exemplary embodiment shown in the drawings has one fenestration, those skilled in the art will appreciate that the drape may have multiple fenestrations. For multiple fenestrations, the absorbent sheet 20 and base sheet 60 may have multiple openings having a plurality of transparent sheets having one or more fenestrations. Accordingly, while the present invention has been described herein in relation to several embodiments, the foregoing disclosure is not intended or to be construed to limit the present invention or otherwise to exclude any such other embodiments, arrangements, variations, or modifications and equivalent arrangements. Rather, the present invention is limited only by the claims appended hereto and the equivalents thereof.

What is claimed is:

1. A surgical drape comprising:
   a base sheet having an upper surface, a lower surface, and at least one opening;
   an absorbent sheet being positioned on the upper surface of said base sheet and having at least one opening aligned with the opening of said base sheet; and
   a transparent sheet attached to said opening of said base sheet and said absorbent sheet, wherein a fenestration is formed in the transparent sheet through which a surgical procedure may be performed when the drape is covering a patient.

2. The surgical drape of claim 1 wherein said absorbent sheet comprises non-woven fabric.

3. The surgical drape of claim 1 wherein said base sheet comprises polyethylene.

4. The surgical drape of claim 1 wherein said transparent sheet is hydrophobic.

5. The surgical drape of claim 1 wherein said transparent sheet comprises a low-density polyethylene film.

6. The surgical drape of claim 1 further comprising a layer of adhesive on a lower surface of said transparent sheet substantially surrounding said fenestration.

7. The surgical drape of claim 6 wherein said adhesive layer comprises a pressure-sensitive biologically acceptable adhesive.

8. The surgical drape of claim 7 wherein said release liner comprises wax-coated paper, silicone-coated paper or plastic materials having at least one non-adherent surface.

9. The surgical drape of claim 7 wherein said release liner is segmented.

10. The surgical drape of claim 7 wherein said release liner is removed and said surgical drape is placed over a patient so that said fenestration is placed over a surgery site.

11. The surgical drape of claim 6 further comprising a release liner on said adhesive layer.

12. The surgical drape of claim 6 wherein said adhesive sticks to the skin of a patient.

13. The surgical drape of claim 1 wherein said absorbent sheet is attached to said base sheet by an adhesive, stitching, thermal bonding or ultrasonic bonding.

14. The surgical drape of claim 1 further comprising instructions printed stamped or adhered to a surface of said drape to indicate how the drape is to be placed on the patient.

15. A surgical drape comprising:
    an opaque absorbent sheet surrounding a clear sheet having a fenestration, wherein said clear sheet has an adhesive coating on at least a portion of said clear sheet surrounding said fenestration.

16. The surgical drape of claim 15 wherein a release liner is on said adhesive coating.

17. The surgical drape of claim 16 wherein said release liner is segmented.

18. The surgical drape of claim 15 wherein said absorbent sheet comprises non-woven fabric.

19. The surgical drape of claim 15 wherein said clear sheet comprises a low-density polyethylene film.

20. The surgical drape of claim 15 wherein said drape has a plurality of fenestrations.

21. A surgical drape comprising:
    an absorbent outer layer having at least one opening;
    an inner layer, adapted to contact a patient having at least one opening aligned with said opening of said absorbent outer layer; and
    a transparent sheet having at least one fenestration attached to said at least one opening.

22. A surgical drape comprising:
    a clear base sheet having an upper surface, a lower surface and a fenestration; and
    an opaque absorbent sheet having an opening attached to said upper surface of said base sheet, wherein said fenestration and at least a portion of said base sheet are exposed through said opening.

* * * * *